United States Patent [19]

Carter et al.

[11] Patent Number: 4,705,688

[45] Date of Patent: Nov. 10, 1987

[54] ANTIBIOTIC LL-E19020 α AND β

[75] Inventors: Guy T. Carter; Michael Greenstein, both of Suffern; Joseph J. Goodman, Spring Valley; Donald B. Borders, Suffern, all of N.Y.; William M. Maiese, Bridgewater; Raymond T. Testa, Cedar Grove, both of N.J.

[73] Assignee: American Cyanamid Company, Stamford, Conn.

[21] Appl. No.: 880,230

[22] Filed: Jun. 30, 1986

[51] Int. Cl.[4] .................. A61K 35/74; C12P 1/06
[52] U.S. Cl. .................................. 424/122; 435/169
[58] Field of Search ..................... 424/122; 435/169

Primary Examiner—Jerome D. Goldberg
Attorney, Agent, or Firm—Alice C. Brennan

[57] ABSTRACT

This invention relates to antibiotic LL-E19020α and LL-E19020β derived from the microorganism *Streptomyces lydicus* subspecies *tanzanius* NRRL 18036, which are useful as an antibacterial agent.

8 Claims, 8 Drawing Figures

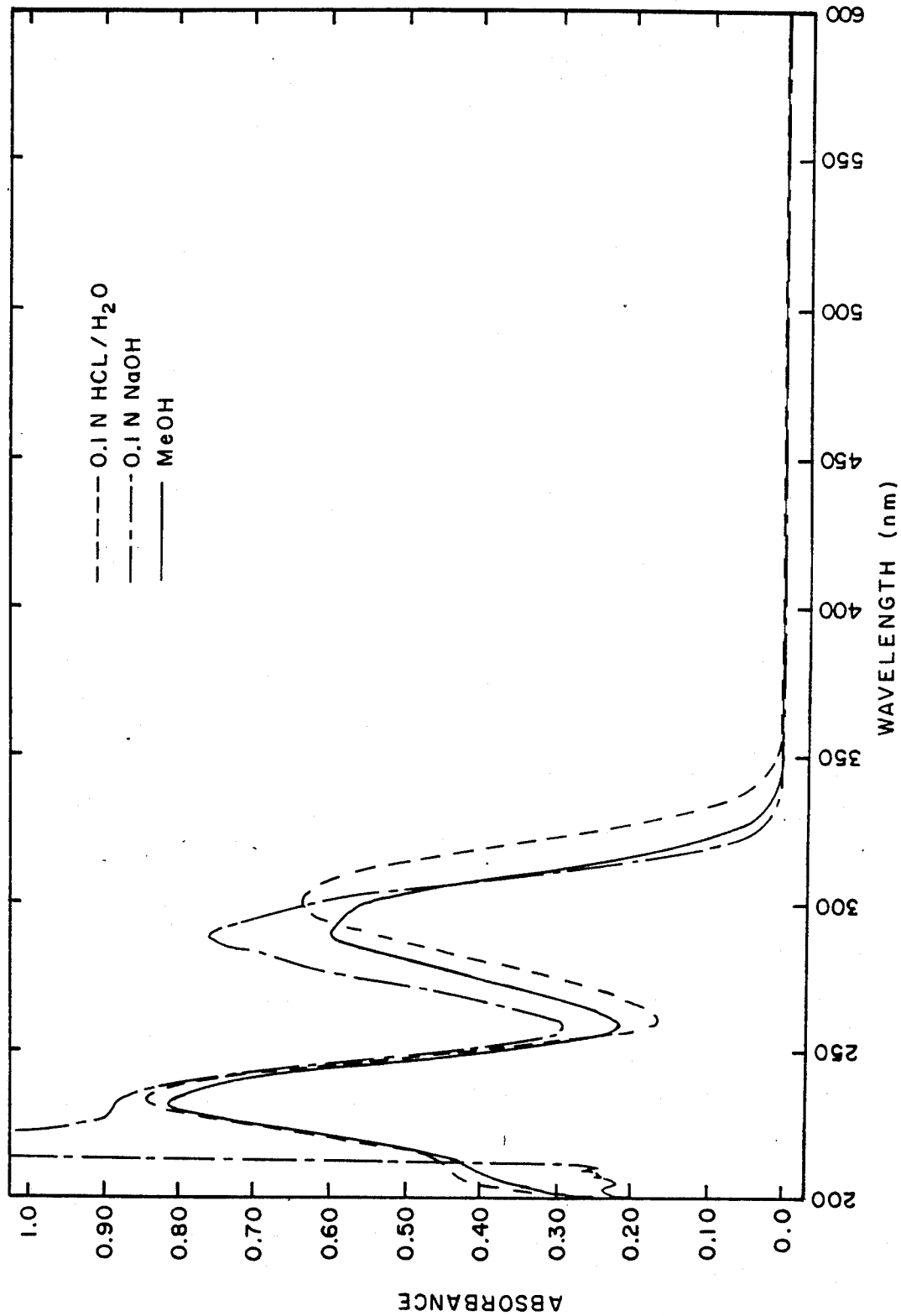

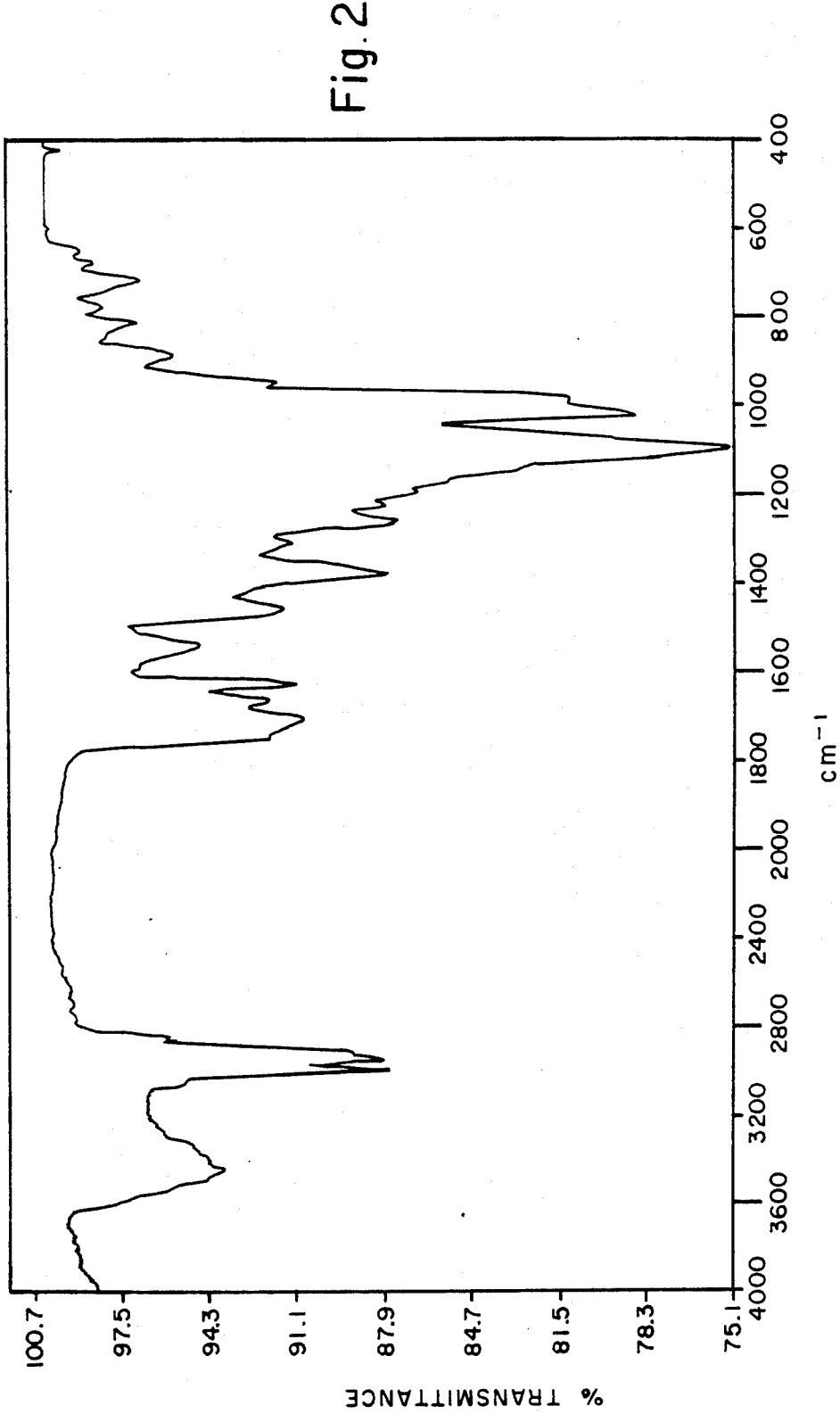

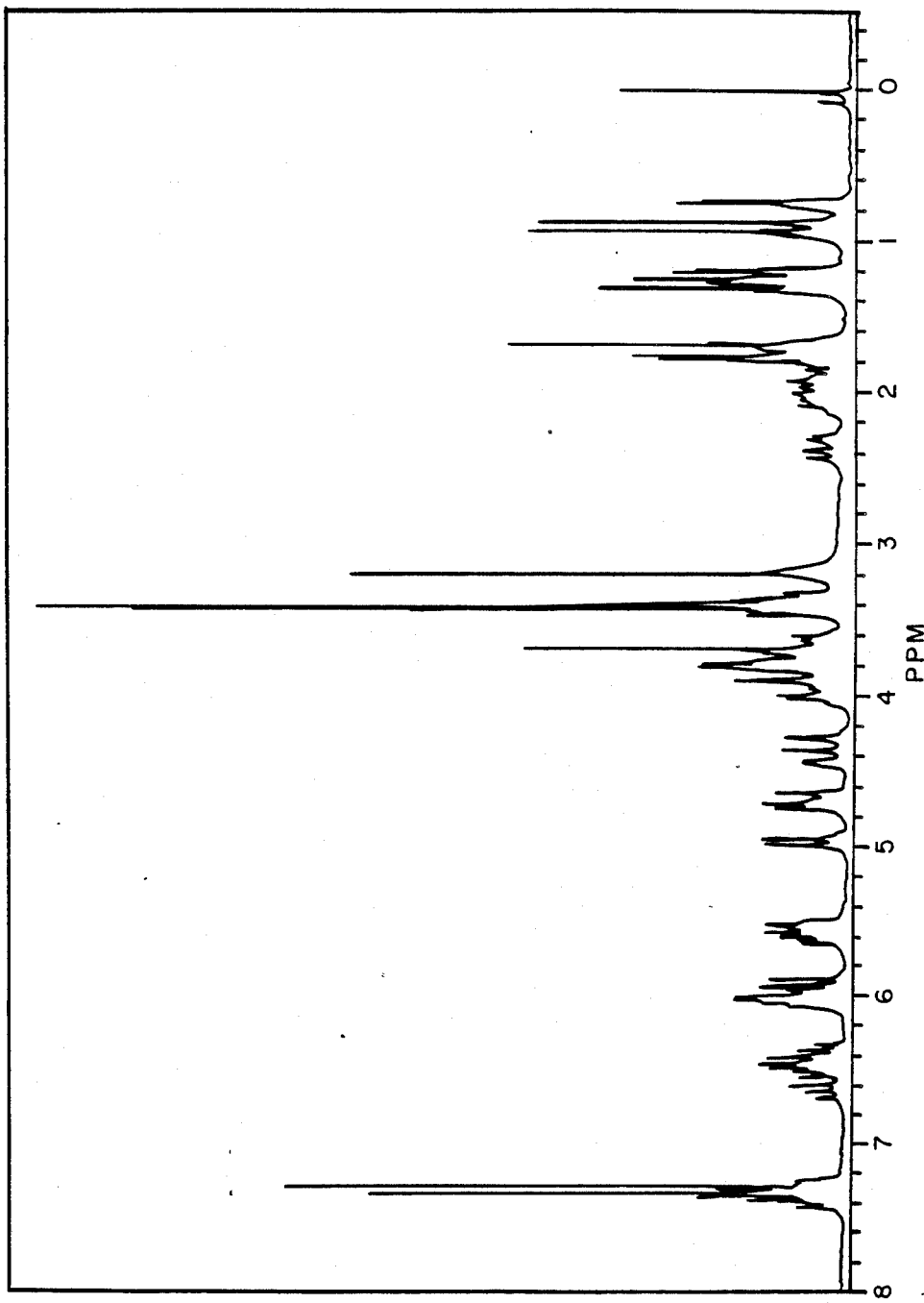

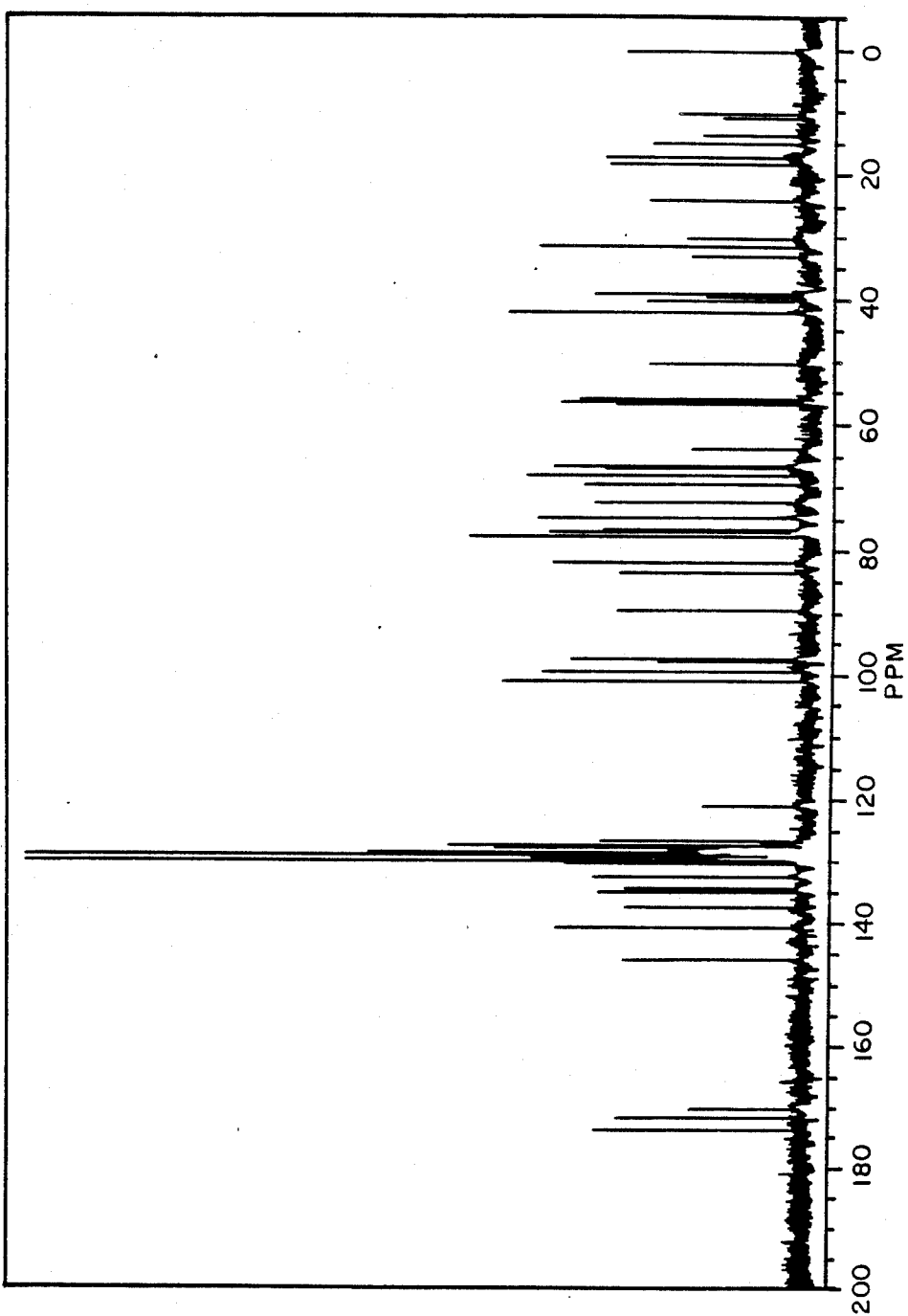

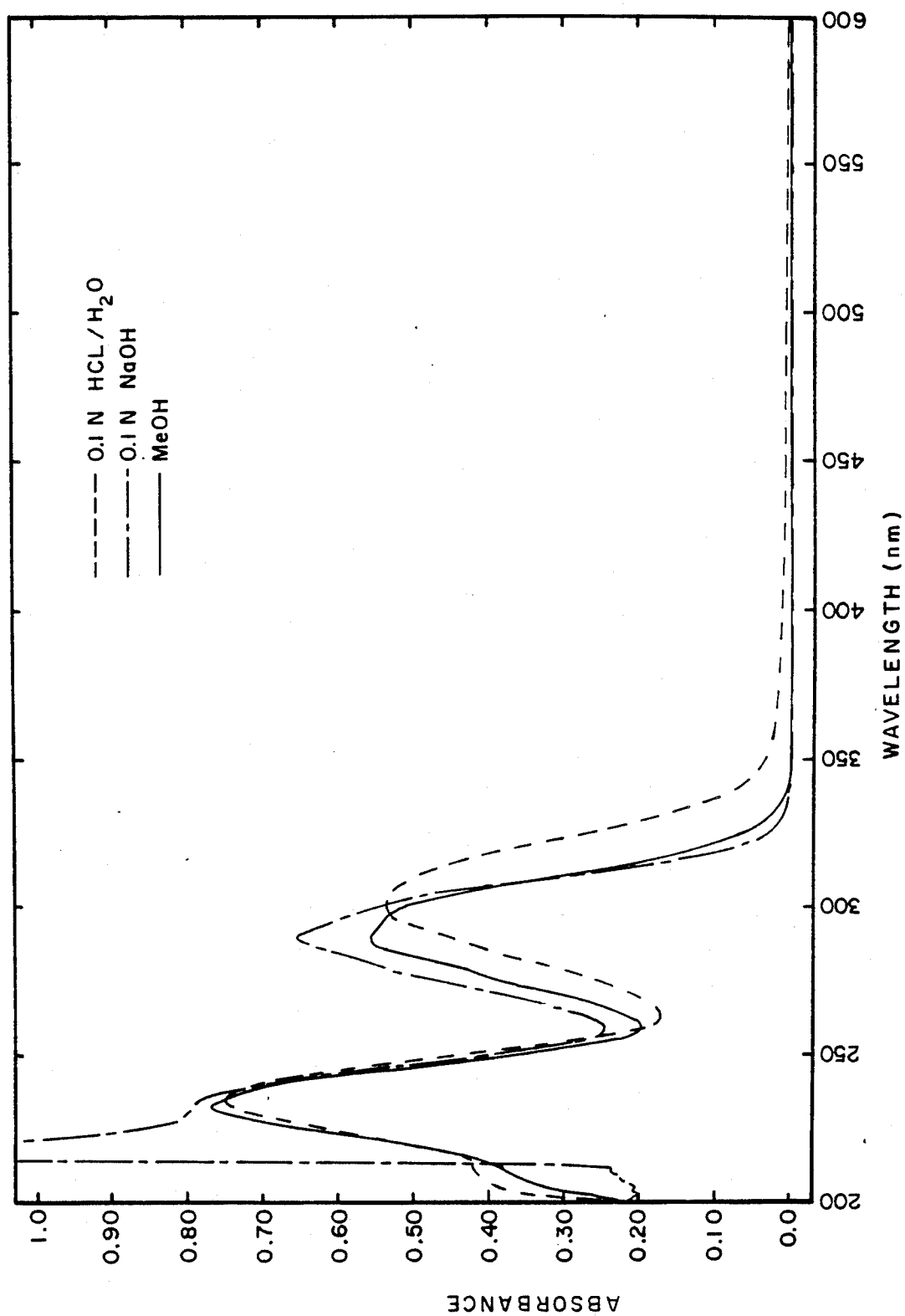

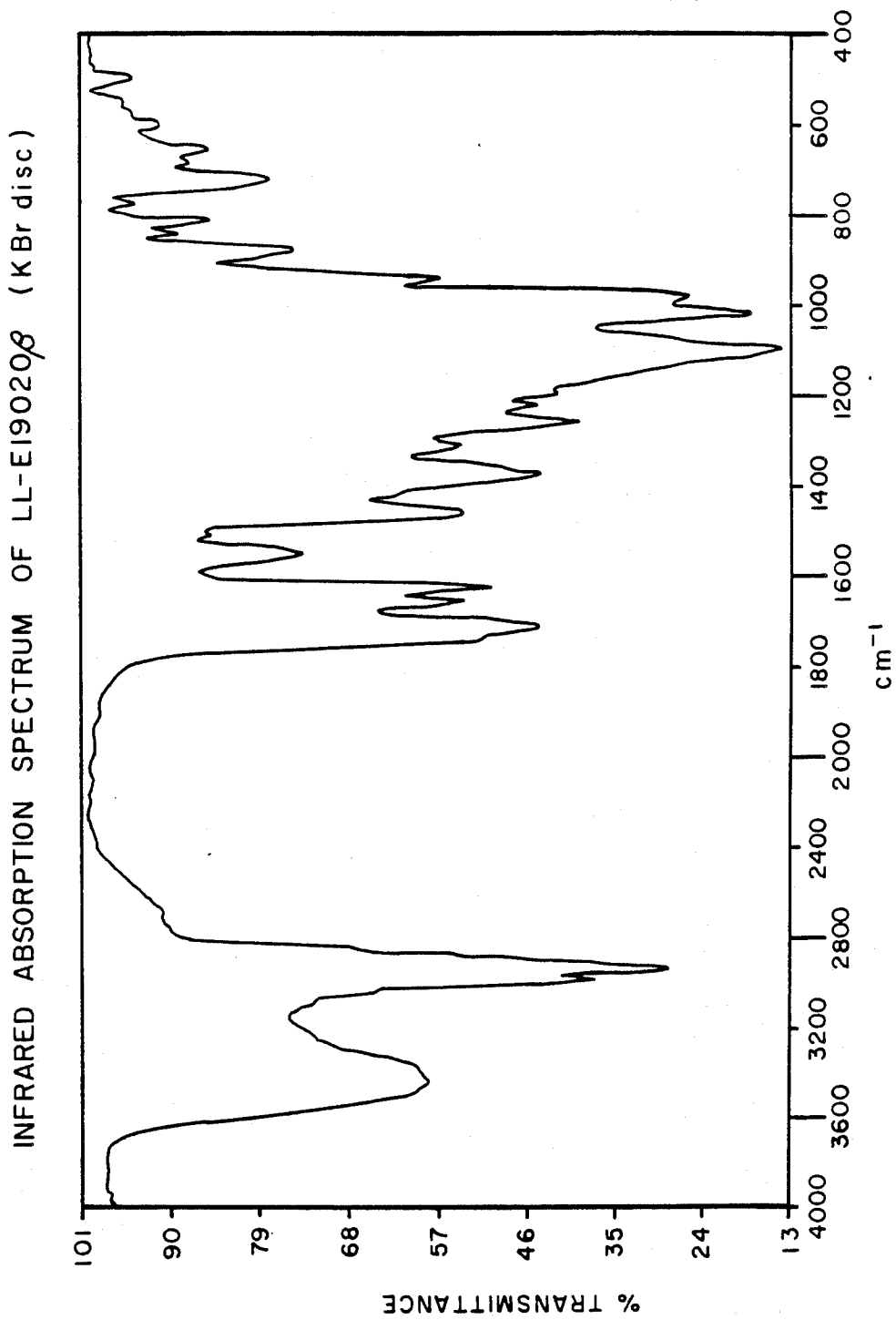

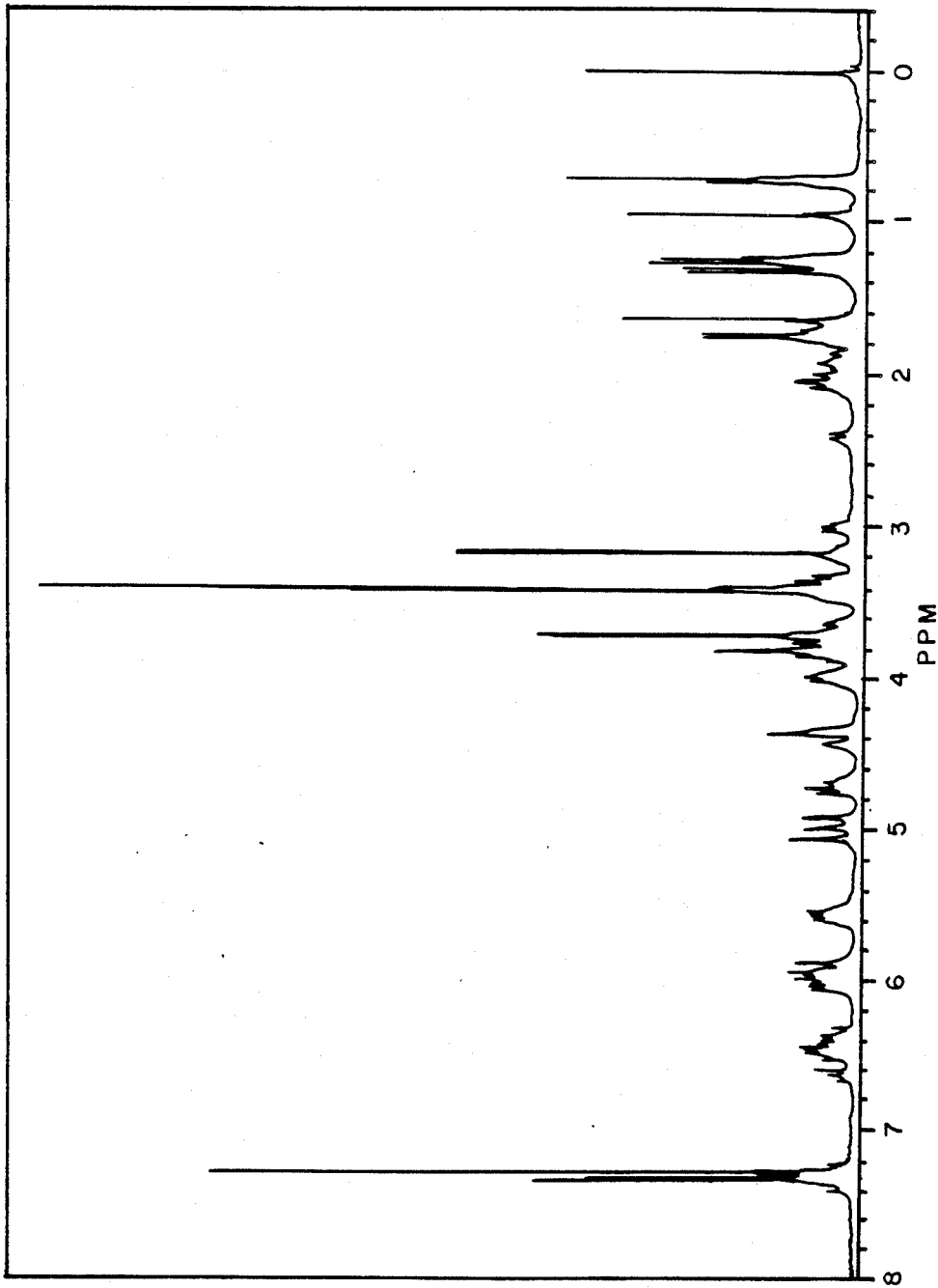

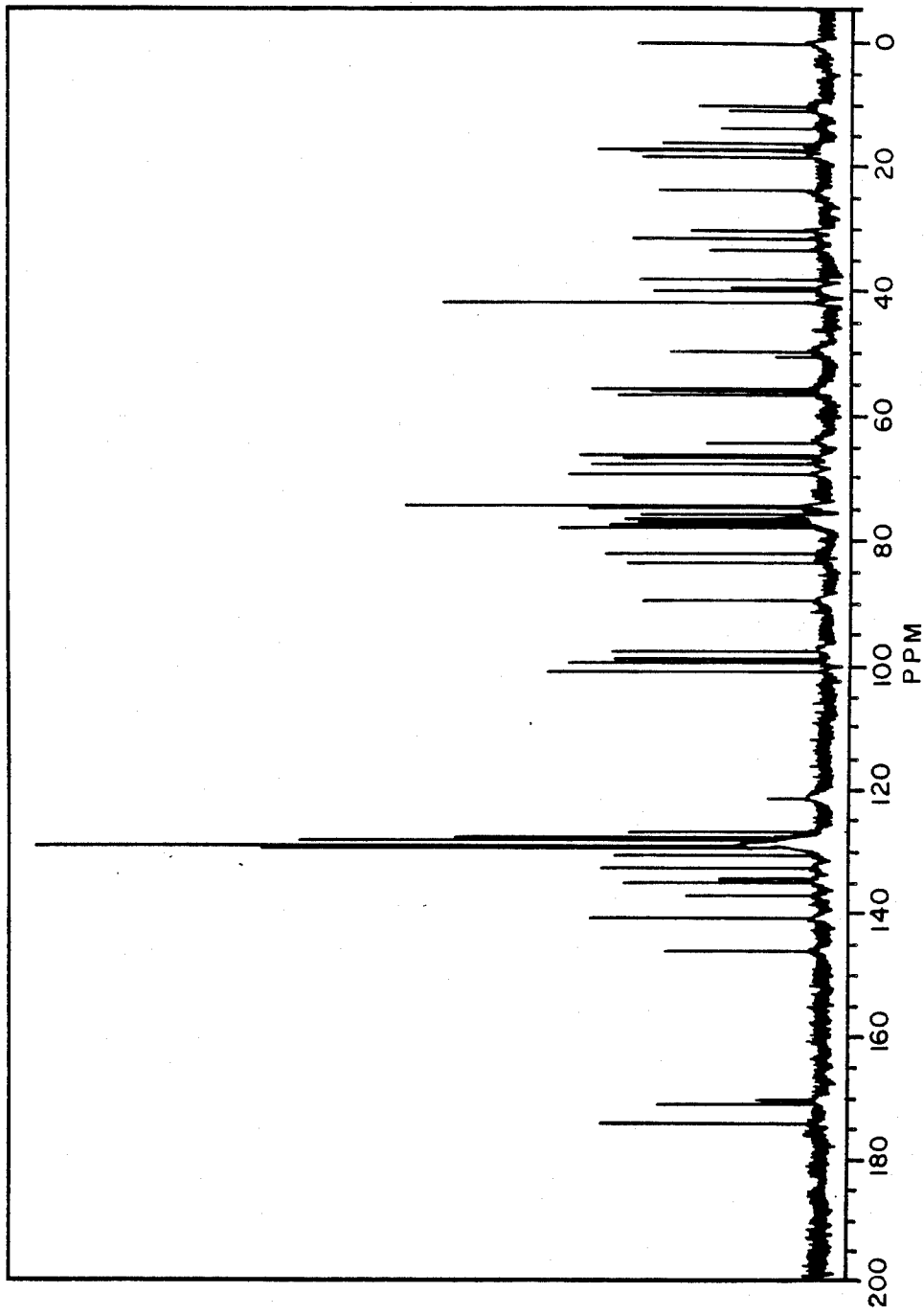

ANTIBIOTIC LL-E19020 α AND β

SUMMARY OF THE INVENTION

This invention relates to new antibacterial agents designated LL-E19020α and LL-E19020β, to their production by fermentation, to methods for their recovery and concentration from crude solutions and to processes for their purification. The present invention includes within its scope the agents in dilute form, as crude concentrates, as a complex of all components, in pure form as individual components and a novel strain of Streptomyces.

The antibiotics LL-E19020α and LL-E19020β are also growth promoters; antiprotozoan agents and anthelmintic agents as described in the respective applications of S. Kantor; S. Kantor and R. L. Kennett, Jr.; and I. B. Wood and M. E. Doscher; filed concurrently herewith and incorporated herein by reference thereto.

BRIEF DESCRIPTION OF THE DRAWINGS

FIG. I shows ultraviolet absorption spectra of LL-E19020α.

FIG. II shows an infrared absorption spectrum of LL-E19020α.

FIG. III shows a proton nuclear magnetic resonance spectrum of LL-E19020α.

FIG. IV shows a carbon-13 nuclear magnetic resonance spectrum of LL-E19020α.

FIG. V shows ultraviolet absorption spectra of LL-E19020β.

FIG. VI shows an infrared absorption spectrum of LL-E19020β.

FIG. VII shows a proton nuclear magnetic resonance spectrum of LL-E19020β.

FIG. VIII shows a carbon-13 nuclear magnetic resonance spectrum of LL-E19020β.

DESCRIPTION OF THE PREFERRED EMBODIMENTS

The structures of antibiotics LL-E19020α and β have not been elucidated but they are described below in conjunction with their physico-chemical characteristics:

The physico-chemical characteristics of LL-E19020α are as follows:

LL-E19020α

1. Approximate elemental analysis: C 62.73; H 7.60; N 1.00; O 28.67 (by difference);
2. Molecular weight: 1225 (FABMS);
3. Apparent molecular formula: $C_{64}H_{91}NO_{22}$;
4. Specific rotation: $[\alpha]_D^{26} = 0$ (C 0.385, methanol);
5. Ultraviolet absorption spectra: as shown in FIG. I

| | |
|---|---|
| $UV_{MAX}^{CH_3OH}$ = | 233 nm (ε 49,800) |
| | 290 nm (ε 36,600) |
| $UV_{MAX}^{0.1N\ HCl}$ = | 234 nm (ε 51,500) |
| | 300 nm (ε 38,900) |
| $UV_{MAX}^{0.1N\ NaOH}$ = | 217 nm (ε 82,700) |
| | 290 nm (ε 45,900) |

6. Infrared absorption spectrum: as shown in FIG. II (KBr disc): 3420, 2970, 2925, 1717, 1695, 1647, 1617, 1525, 1445, 1365, 1092, 1018 cm$^{-1}$;
7. Proton nuclear magnetic resonance spectrum: as shown in FIG. III (300 MHz, CDCl$_3$);
8. Carbon-13-nuclear magnetic resonance spectrum: as shown in FIG. IV (75 MHz, CDCl$_3$, ppm downfield from TMS), significant peaks as listed below:

| | | | | | |
|---|---|---|---|---|---|
| 173.3 | 129.0 | 97.3 | 74.2 | 55.4 | 17.2 |
| 171.4 | 128.6 (2x) | 97.0 | 72.0 | 49.8 | 17.0 |
| 170.1 | 128.43 | 89.2 | 71.9 | 41.8 | 14.8 |
| 145.7 | 128.38 | 83.3 | 69.1 | 39.8 | 13.5 |
| 140.3 | 128.1 (2x) | 81.6 | 67.5 | 39.1 | 10.8 |
| 137.0 | 127.5 | 77.6 | 66.4 | 38.8 | 10.0 |
| 134.4 | 127.1 | 77.0 | 66.1 | 32.9 | |
| 133.9 | 126.3 | 76.4 | 63.5 | 31.0 | |
| 132.0 | 120.8 | 74.6 | 56.5 | 29.9 | |
| 130.1 | 100.6 | 74.5 | 56.0 | 23.8 | |
| 129.5 (2x) | 99.0 | 74.4 | 55.6 | 18.1 | |

2x = two overlapping signals

LL-E19020β

1. Approximate elemental analysis: C 63.33; H 7.72; N 1.16; O 27.79 (by difference);
2. Molecular weight: 1225 (FABMS);
3. Apparent molecular formula: $C_{64}H_{91}NO_{22}$;
4. Specific rotation: $[\alpha]_D^{26} = -17 \pm 2$ (C 0.455, methanol);
5. Ultraviolet absorption spectra: as shown in FIG. V

| | |
|---|---|
| $UV_{MAX}^{CH_3OH}$ = | 233 nm (ε 47,000) |
| | 290 nm (ε 34,100) |
| $UV_{MAX}^{0.1N\ HCl}$ = | 234 nm (ε 46,000) |
| | 301 nm (ε 32,800) |
| $UV_{MAX}^{0.1N\ NaOH}$ = | 217 nm (ε 77,800) |
| | 290 nm (ε 39,700) |

6. Infrared absorption spectrum: as shown in FIG. VI (KBr disc): 3430, 2970, 2930, 1712, 1648, 1620, 1543, 1454, 1367, 1265 1098, 1020, 980 cm$^{-1}$;
7. Proton nuclear magnetic resonance spectrum: as shown in FIG. VII (300 MHZ, CDCl$_3$);
8. Carbon-13 nuclear magnetic resonance spectrum, as shown in FIG. VIII (75 MHz, CDCl$_3$, ppm downfield TMS), significant peaks as listed below:

| | | |
|---|---|---|
| 173.6 | 99.0 | 55.4 |
| 170.6 | 98.4 | 49.6 |
| 170.0 | 97.2 | 41.6 (2x) |
| 145.6 | 89.2 | 39.8 |
| 140.2 | 83.3 | 39.1 |
| 136.7 | 81.6 | 38.0 |
| 134.4 | 77.6 | 32.9 |
| 133.9 | 77.5 | 31.1 |
| 132.0 | 76.2 | 29.9 |
| 130.1 | 75.5 | 23.7 |
| 129.1 (2x) | 74.6 | 18.1 |
| 128.9 | 74.5 | 17.2 |
| 128.6 (2x) | 74.2 | 17.0 |
| 128.5 | 69.1 | 16.2 |
| 128.4 | 68.9 | 13.5 |
| 128.3 | 67.5 | 10.8 |
| 128.2 | 66.6 | 10.0 |
| 127.8 | 66.1 | |
| 127.2 | 64.1 | |
| 126.5 | 56.5 | |
| 120.9 | 56.0 | |
| 100.6 | 55.6 | |

2x = two overlapping signals

The new antibacterial agents LL-E19020α and LL-E19020β are formed during the cultivation under controlled conditions of a new strain of *Streptomyces lydicus* ssp. *tanzanius*.

This microorganism is maintained in the culture collection of the Medical Research Division, American Cyanamid Company, Pearl River, NY as culture number LL-E19020. A viable culture of this new microorganism has been deposited with the Patent Culture Collection Laboratory, Northern Regional Research Center, U.S. Department of Agriculture, Peoria, Ill. 61604, and has been added to its permanent collection. It has been assigned the strain designation NRRL 18036 by said depository. Access to said culture, under strain designation NRRL 18036, during pendency of the instant application shall be available to one determined by the Commissioner of Patents and Trademarks to be entitled thereto under 37 C.F.R. §1.14 and 35 U.S.C. §122, and all restrictions on availability to the public of such culture will be irrevocably removed upon grant of a patent on the instant application.

Culture LL-E19020 was isolated from a soil sample taken in a pasture near Lake Manyara, Tanzania, Africa.

Culture LL-E19020 produces short spiral spore chains, 10–50 spores long, with occasional longer chains. These tend to coalesce to form dry blackish masses on such ISP media as oatmeal and inorganic salts-starch. The spores have smooth surfaces as assessed by electron microscopy. The strain contains the L isomer of diaminopimelic acid, and may thus be assigned to the genus Streptomyces.

In the ISP tests for utilization of carbohydrates, LL-E19020 shows growth on arabinose, fructose, inositol, mannitol, raffinose, rhamnose, sucrose and xylose. Cellulose is not utilized.

The reactions of LL-E19020 in the Gordon physiological series are compared in the following Table I with those of *Streptomyces lydicus* ISP 5461 which it most closely resembles morphologically and physiologically.

Because LL-E19020 differs from ISP 5461 in five characteristics (xanthine hydrolysis, decarboxylation of oxalate, acid from erythritol, rhamnose and β-methyl-D-xyloside) it is designated as a subspecies of *Streptomyces lydicus*.

TABLE I

| Gordon Test Reactions of LL-E19020 and *Streptomyces lydicus* ISP 5461 | | |
|---|---|---|
| Reaction | LL-E19020 | ISP 5461 |
| Degradation/Transformation of | | |
| Casein | + | + |
| Xanthine | − | + |
| Hypoxanthine | + | + |
| Tyrosine | + | + |
| Adenine | + | + |
| Production of | | |
| Amylase | + | + |
| Gelatinase | + | + |
| Phosphatase | + | + |
| Nitrate Reductase | − | − |
| Urease | + | + |
| Esculinase | + | + |
| Growth on/in | | |
| 5% Sodium chloride | + | + |
| Salicylate | − | − |
| Lysozyme Broth | trace | trace |
| Utilization of | | |
| Acetate | + | + |
| Benzoate | − | − |
| Citrate | + | + |
| Lactate | + | + |
| Malate | + | + |
| Mucate | + | + |
| Oxalate | + | − |
| Propionate | + | + |
| Pyruvate | + | + |
| Succinate | + | + |
| Tartrate | − | − |
| Growth at | | |
| 10° C. | + | + |
| 42° C. | − | − |
| 50° C. | − | − |
| Acid from | | |
| Adonitol | + | + |
| Arabinose | + | + |
| Cellobiose | + | + |
| Dextrin | + | + |
| Dulcitol | − | − |
| Erythritol | + | − |
| Fructose | + | + |
| Galactose | + | + |
| Glucose | + | + |
| Glycerol | + | + |
| Inositol | + | + |
| Lactose | + | + |
| Maltose | + | + |
| Mannitol | + | + |
| Mannose | + | + |
| Melibiose | + | + |
| α-Methyl-D-Glucoside | + | + |
| Raffinose | + | + |
| Rhamnose | + | − |
| Salicin | + | + |
| Sorbitol | + | + |
| Sucrose | + | + |
| Trehalose | + | + |
| Xylose | + | + |
| β-Methyl-D-Xyloside | + | − |

It is to be understood that for the production of these new antibacterial agents the present invention is not limited to this particular organism or to organisms fully answering the above characteristics which are given for illustrative purposes only. In fact, it is desired and intended to include the use of mutants produced from this organism by various means such as exposure to X-radiation, ultraviolet radiation, N′-methyl-N′-nitro-N-nitrosoguanidine, actinophages and the like.

The in vitro antibacterial activity of LL-E19020α and β was determined against a spectrum of gram-positive and gram-negative bacteria by a standard agar dilution method. Mueller-Hinton agar containing 5% sheep blood and two-fold decreasing concentrations of either LL-E19020α or β were poured into petri dishes. The agar surfaces were inoculated with 1 to $5 \times 10^4$ colony forming units of bacteria by means of the Steers replicating device. The lowest concentration of antibiotic that inhibited growth of a bacterial strain after 18 hours incubation was recorded as the minimal inhibitory concentration for that strain. The results are given in Table II.

TABLE II

In vitro Antibacterial Activity of LL-E19020α and β

| Organism | | Minimal Inhibitory Concentration (mcg/ml) | |
|---|---|---|---|
| | | LL-E19020α | LL-E19020β |
| Staphylococcus aureus | ATCC 25923 | >256 | >256 |
| Staphylococcus aureus | Smith | 128 | >128 |
| Staphylococcus aureus | VGH-84-45 | >256 | >128 |
| Staphylococcus aureus | CMC-83-127 | >256 | >128 |
| Staphylococcus aureus | CMC-83-131 | >256 | >128 |
| Staphylococcus aureus | CMC-83-132 | >256 | >128 |
| Staphylococcus aureus | SSC-82-57 | >256 | >128 |
| Staphylococcus epidermidis | IO-83-58 | >256 | >128 |
| Staphylococcus saprophyticus | VGH-84-50 | >256 | >128 |
| Streptococcus sp. (β-hemolytic) | C203 | 0.5 | 0.5 |
| Streptococcus sp. (β-hemolytic) | VGH-84-60 | 0.25 | 0.25 |
| Streptococcus sp. (β-hemolytic) | VGH-84-61 | 1 | 0.5 |
| Streptococcus sp. (β-hemolytic) | VGH-84-62 | 1 | 0.5 |
| Streptococcus sp. (β-hemolytic) | VGH-84-63 | 0.12 | 0.12 |
| Streptococcus sp. (β-hemolytic) | VGH-84-64 | 0.12 | 0.12 |
| Streptococcus pneumoniae | SVI | 1 | 1 |
| Streptococcus pneumoniae | K-84-21 | 1 | 0.5 |
| Streptococcus pneumoniae | VGH-84-56 | 1 | 0.5 |
| Streptococcus pneumoniae | VGH-84-57 | 2 | 1 |
| Streptococcus pneumoniae | VGH-84-58 | 0.25 | 0.25 |
| Streptococcus pneumoniae | VGH-84-59 | 0.25 | 0.25 |
| Enterococcus | VGH-84-65 | 256 | >128 |
| Enterococcus | VGH-84-68 | >256 | >128 |
| Enterococcus | IO-83-28 | >256 | >128 |
| Enterococcus | IO-83-40 | >256 | >128 |
| Enterococcus | CMC-83-72 | >256 | >128 |
| Escherichia coli | 311 | >256 | >128 |
| Klebsiella pneumoniae | AD | >256 | >128 |
| Enterobacter cloacae | VGH-84-37 | >256 | >128 |
| Morganella morganii | VGH-84-71 | >256 | >128 |
| Serratia marcescens | K-84-18 | >256 | >128 |
| Pseudomonas aeruginosa | 12-4-4 | >256 | >128 |
| Bacteroides fragilis | NYC 77-1 | >128 | >128 |
| Clostridium difficile | ATCC 17858 | 4 | 1 |
| Clostridium perfringens | ATCC 13124 | 16 | 4 |
| Peptococcus magnus | ATCC 29328 | 0.12 | 0.5 |
| Peptococcus magnus | ATCC 14956 | 0.12 | 0.5 |

The in vivo antibacterial activity of antibiotics LL-E19020α and β was established by infecting female CD-1 mice from Charles River Laboratories, weighing 20±2 g each, intraperitoneally with either $1.7 \times 10^2$ CFU/0.5 ml of broth of *Streptococcus pyogenes* C203 or $6.5 \times 10^5$ CFU/0.5 ml of broth of *Staphylococcus aureus* Smith. The mice were treated subcutaneously, 30 minutes before infection with the indicated dose of the test compound in 0.5 ml of 0.2% aqueous agar. The results of this test appear in Table III.

TABLE III

In vivo Activity of LL-E19020α and β

| Single Subcutaneous Dose (mg/kg) | Survival Ratios 7 Days After Injection | | | |
|---|---|---|---|---|
| | S. pyogenes C203 | | S. aureus Smith | |
| | LL-E19020α | LL-E19020β | LL-E19020α | LL-E19020β |
| 256 | NT | NT | 3/5 | 1/5 |
| 64 | 5/5 | 5/5 | 3/5 | 1/5 |
| 32 | 5/5 | 5/5 | NT | NT |
| 16 | 5/5 | 5/5 | 3/5 | 1/5 |
| 8 | 4/5 | 3/5 | NT | NT |
| 4 | 2/5 | 2/5 | 2/5 | 1/5 |
| Non-treated infected controls | 0/10 | 0/10 | 0/10 | 0/10 |

NT = not tested

Antibiotics LL-E19020α and LL-E19020β derive their utility from their antibacterial activity. For example, these antibiotics may be used in the suppression of bacterial infections, as a topical antibacterial agent and as a general disinfectant for laboratories.

In addition to their antibacterial activity these compounds are effective as anticoccidial agents in poultry and as growth promotants and anthelmintic agents. These utilities are the subject of patent applications filed concurrently herewith and incorporated herein by reference.

In therapeutic use, the compounds of this invention may be administered in the form of conventional pharmaceutical compositions appropriate for the intended use. Such composition may be formulated so as to be suitable for oral, parenteral, or topical administration. The active ingredient may be combined in admixture with a nontoxic pharmaceutically acceptable carrier, which carrier may take a wide variety of forms, depending on the form of preparation desired for administration, ie, oral, parenteral or topical.

GENERAL FERMENTATION CONDITIONS

Cultivation of *Streptomyces lydicus* ssp. *tanzanius* NRRL 18036 may be carried out in a wide variety of liquid culture media. Media which are useful for the production of LL-E19020α and LL-E19020β include an assimilable source of carbon, such as dextrin, sucrose, molasses, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

GENERAL PROCEDURE FOR THE ISOLATION OF LL-E19020α AND β

The LL-E19020α and LL-E19020β are recovered from the fermentation broth by pH adjustment to 4.5–5.5, filtration through diatomaceous earth, extraction into a solvent such as ethyl acetate, concentration, dissolution in a solvent such as dichloromethane and purification by column chromatography on silica gel using successively, dichloromethane and methanol:dichloromethane (1:4), giving a crude product.

The crude product is then separated into the α and β components and further purified by high performance liquid chromatography on a reverse-phase column using the system acetonitrile, 0.1M ammonium acetate buffer pH 4.3 (1:1).

The invention will be further described in conjunction with the following non-limiting examples.

EXAMPLE 1

Inoculum Preparation

A typical medium used to grow the primary inoculum was prepared according to the following formula:

| | |
|---|---|
| Dextrose | 1.0% |
| Dextrin | 2.0% |
| Yeast extract | 0.5% |
| NZ Amine A ®[1] | 0.5% |
| Calcium carbonate | 0.1% |
| Water qs | 100.0% |

[1][A pancreatic digest of casein, registered trademark of Sheffield Chemical, Norwich, NY]

This medium was adjusted to pH 7.0 and then sterilized. A 100 ml portion of this sterile medium in a 500 ml flask, was inoculated with mycelial scrapings from an agar slant of *Streptomyces lydicus* ssp. *tanzanius* NRRL 18036. The medium was then placed on a rotary shaker and incubated at 28° C. for 48 hours. This primary inoculum was then used to inoculate 10 liters of the same sterile medium in a bottle. This medium was grown for 24 hours providing secondary inoculum. This secondary inoculum was then used to inoculate 250 liters of the same sterile medium in a tank. This medium was grown at 28° C. for 48 hours with a sterile air flow of 200 liters per liter of mash per minute and agitation by an impeller driven at 220 rpm, providing tertiary inoculum.

EXAMPLE 2

Fermentation

A fermentation medium of the following formulation was prepared:

| | |
|---|---|
| Dextrin | 3.0% |
| Molasses | 2.0% |
| Soy peptone | 0.75% |
| Yeast extract | 0.25% |
| Calcium carbonate | 0.2% |
| Water qs | 100.0% |

This medium was sterilized and 2700 liters was then inoculated with 300 liters of tertiary inoculum from Example 1. The fermentation was conducted at 28° C., with a sterile air flow of 0.55 liters of air per liter of mash per minute and agitation by an impeller driven at 100 rpm for 113 hours, at which time the mash was harvested.

EXAMPLE 3

Isolation and Purification of LL-E19020α and β

The harvest mash from two fermentations conducted as described in Example 2 were combined, making a total of 6000 liters, adjusted to pH 5 with hydrochloric acid and filtered through diatomaceous earth. The filtrate was extracted with ethyl acetate and the extract concentrated to a syrup.

This syrup was dissolved in dichloromethane and applied to 1000 g of silica (60–200 mesh) on a sintered glass funnel. The silica column was first eluted with dichloromethane, collecting four 2 liter fractions and then with methanol:dichloromethane (1:4) collecting a 4 liter fraction. This 4 liter fraction was evaporated to dryness, giving 120 g of residue. The residue was redissolved in 4 liters of dichloromethane and applied to 500 g of silica on a sintered glass funnel. The silica was eluted with methanol:dichloromethane (1:4) collecting 2 liter fractions. Fractions 1 and 2 were combined and evaporated, giving 99 g of crude LL-E19020α and β.

This crude product was dissolved in methanol and applied to a 12 liter reverse-phase column (C18 bonded phase 40 micron). The column was eluted with acetonitrile, 0.1M ammonium acetate buffer pH 4.3 (1:1) at a rate of 1.0 liter per minute. Thirteen 24 liter fractions were collected. Fraction 7 contained LL-E19020α and fractions 11–13 contained LL-E19020β.

The antibiotics were extracted from the mobile phase using dichloromethane followed by evaporation and freeze drying from t-butanol, giving 10 g of LL-E19020α and 14 g of LL-E19020β, both as white solids.

EXAMPLE 4

Pasteurella Disk Test

Sterile paper disks (¼" in diameter) are soaked in a 2.5 mg/ml solution of test compound and dried in a 37° C. incubator overnight. Standard antibiotic control disks are prepared for testing along with the test compound disks. The dried disks are stored at 2°–4° C. until used. Two test organisms, *Pasteurella multocida* 31081B and *Pasteurella haemolytica* 30660, are cultured in brain heart infusion broth for 5 hours at 37° C. A 1:10 dilution of each culture is made in Mueller-Hinton broth. Two hundred milliliters of Mueller-Hinton agar are seeded with 1 ml of the diluted culture and aseptically poured into 9 inch×9 inch bioassay plates manufactured by Nunc. Use of the 9"×9" plates permits the testing of 36 disks per plate. Appropriate disks are applied to the seeded agar plates and incubated for 18–20 hours at 37° C. Zones of inhibition are recorded.

*T. Hyodysenteriae* Disk Test

Sterile paper disks ($\frac{1}{4}$" in diameter) are soaked in a 2.5 mg/ml solution of a test compound and dried in a 37° C. incubator overnight. Standard antibiotic control disks are prepared for testing along with the test compound disks. The dried disks are stored at 2°–4° C. until used. Two *T. hyo.* strains, B78 (ATCC 27164) and B204 (ATCC 31212), are cultured for 24 hours at 38° C. in Hungate culture tubes containing 5 ml brain heart infusion broth supplemented with 2% fetal calf serum (prepared anaerobically). Two hundred milliliters of trypticase soy agar, containing 5% defibrinated bovine blood, are seeded with 1 ml of culture and aseptically poured into 9"×9" bioassay plates manufactured by Nunc. Use of the 9"×9" plates permit the testing of 36 disks per plate. Appropriate disks are applied to the agar plates which are then incubated for 24–48 hours at 38° C. in an anaerobic chamber containing 80% nitrogen, 10% carbon dioxide, and 10% hydrogen until hemolysis is complete. Zones of inhibited hemolysis are recorded.

Minimum Inhibitory Concentration Procedure by Agar Dilution

1. Serial two-flow dilutions of drug are prepared in Mueller-Hinton broth in a range of 2560 µg/ml–0.15 µg/ml plus a solvent control.
2. Two milliliters of drug dilution (10X) are added to sterile screwcap bottles to which 18 ml of Mueller-Hinton agar containing 5.6% defibrinated sheep blood is added. Final drug concentration ranges 256 µg/ml–0.015 µg/ml in agar containing 5% sheep blood.
3. A few isolated colonies of each test organism are inoculated into 5 ml trypticase soy broth or brain heart infusion broth. The cultures are shaken at 35° C. for 5 hours.
4. Each culture is diluted 1:50 ($10^{-1.7}$) in Mueller-Hinton broth and applied to agar plates using a Steers replicator. Control plates should be seeded last to ensure that viable organisms were present throughout the procedure. Inoculated agar plates are allowed to stand undisturbed until the inoculum spots are completely absorbed.
5. The plates are inverted and incubated at 35° C. for 18 hours without $CO_2$.
6. The minimum inhibitory concentration (MIC) is taken as the lowest concentration of antimicrobial agent at which complete inhibition occurs. A very fine, barely visible haze or a single colony is disregarded.

MIC Test Organisms

*Staphylococcus aureus* ATCC 25923
*Staphylococcus aureus* 52 "Smith strain"
*Staphylococcus aureus* 14 ATCC 6538P
*Staphylococcus aureus* 335 Mastitis isolate
*Staphylococcus aureus* 336 Mastitis isolate
*Staphylococcus aureus* 344 Mastitis isolate
*Staphylococcus aureus* Penicillin resistant
*Streptococcus pyogenes* ATCC 19615
*Streptococcus pyogenes* 41
*Streptococcus agalactiae* 341
*Streptococcus agalactiae* 342
*Streptococcus agalactiae* 343
*Streptococcus dysgalactiae* 340
*Streptococcus faecalis* 42 Dr. Juke's #8043
*Streptococcus uberis* Cornell Mastitis Center
*Escherichia coli* ATCC 25922
*Escherichia coli* 81
*Escherichia coli* 80-654 Tetracycline resistant
*Pasteurella multocida* 31081B (in vitro disk test strain)
*Pasteurella multocida* 80-3548 (in vivo mouse model strain)
*Pasteurella multocida* 31451
*Pasteurella multocida* 32301
*Pasteurella multocida* 30170B
*Pasteurella multocida* 80-5945
*Pasteurella haemolytica* 30660 (in vitro disk test strain)
*Pasteurella haemolytica* L-101 National Animal Disease Center
*Pasteurella haemolytica* 80-6744
*Salmonella choleraesuis* var. Kunzendorf I-3
*Salmonella choleraesuis* var. Kunzendorf 4
*Bordetella bronchiseptica* "B" strain
*Bordetella bronchiseptica* 11266
*Bordetella bronchiseptica* 31068B
*Bordetella bronchiseptica* 11948A

Minumum Inhibitory Concentration Assay for *Mycloplasma gallisepticum*

1. Serial two-fold dilutions of drug stock solutions are prepared in mycoplasma broth in a concentration of 2560 µg/ml–0.015 µg/ml plus a solvent control. These concentrations are 10X the final test concentration.
2. A frozen ($-80°$ C.) stock culture of *Mycoplasma gallisepticum* "R" strain is thawed and a 0.5 ml aliquot is inoculated into 5 ml of mycoplasma culture broth. At the same time, 0.1 ml is plated on to a mycoplasma agar plate as a purity check. Both cultures are incubated at 37° C. Growth in broth is indicated by a color change from red to yellow. Growth on agar is observed with the aid of a stereoscope.
3. The MIC assay is carried out in 96 well microtiter plates. To each test well, 25 µl of 10X drug solution is aliquoted. Appropriate solvent controls are also included.
4. The mycoplasma inoculum is prepared by transferring a positive broth culture to fresh medium using the ratio of 0.2 ml culture:5.0 ml medium. Large amounts of inoculum are prepared as needed using the formula above.
5. A 225 µl aliquot of previously inoculated mycoplasma broth is added to each test well and mixed. A plastic sealer tape is applied and a small hole is placed over the center of each test well using sterile 25 guage needles. To avoid well cross-contamination, needles are changed for each drug. Further, tape puncturing proceeds from lowest to highest concentration of drug. Final test concentration ranges from 256 µg/ml–0.0015 µg/ml with a total volume of 250 µl. Wells containing 250 µl of inoculated medium only and uninoculated medium are added as further controls.
6. The assay plate is incubated at 37° C. until a broth color change from red to yellow first occurs uniformly throughout the test plate. The MIC value is recorded as the concentration at which the broth color (red) remains unchanged.

TABLE IV

ANTIBACTERIAL DATA FOR E19020 ALPHA & E19020 BETA
PRIMARY IN VITRO DISK DIFFUSION TEST

| | ZONE SIZE (mm) | | | |
|---|---|---|---|---|
| | E19020 ALPHA | E19020 BETA | CTC | TIAMULIN |
| Pasteurella multocida 31081B | 15 | 13 | 25 | N/T |
| Pasteurella haemolytica 30660 | 13 | 13 | 11 | N/T |
| Treponema hyodysenteriae B78 (ATCC 27164) | 0 | N/T | 45 | 67 |
| Treponema hyodysenteriae B204 (ATCC 31212) | 15 | 11 | 37 | 70 |

N/T = Not Tested

TABLE V

MINIMUM INHIBITORY CONCENTRATIONS BY AGAR DILUTION

| | MIC (μg/ml) | |
|---|---|---|
| | E19020 ALPHA | E19020 BETA |
| Staphylococcus aureus (7) | ≧256 | 128–≧256 |
| Streptococcus pyogenes (2) | 2 | 2–4 |
| Streptococcus agalactiae (4) | 2–8 | 2–4 |
| Streptococcus faecalis (1) | 8 | 8 |
| Streptococcus uberis (1) | 8 | 4 |
| Escherichia coli (2) | ≧256 | ≧256 |
| Salmonella choleraesuis (2) | >256 | >256 |
| Bordetella bronchiseptica (4) | >256 | >256 |
| Pasteurella multocida (6) | 8–16 | 8–16 |
| Pasteurella haemolytica (3) | 16 | 16 |

NOTE:
Numbers in parentheses indicate the number of strains tested.

TABLE VI

MINIMUM INHIBITORY CONCENTRATION BY MICRODILUTION

| | MIC (μg/ml) | | | | | |
|---|---|---|---|---|---|---|
| | E19020 ALPHA | E19020 BETA | CARBADOX | TIAMULIN | CTC | TYLOSIN |
| Treponema hyodysenteriae B78 (ATCC 27164) | 1 | 1 | 0.5 | 0.015 | N/T | N/T |
| Treponema hyodysenteriae B204 (ATCC 31212) | 1 | 0.5 | 0.25 | 0.015 | N/T | N/T |
| Mycoplasma gallisepticum "R" | 0.125 | 0.125 | N/T | N/T | 0.5 | 0.03 |

N/T = Not Tested

What is claimed is:

1. The compound LL-E19020 ALPHA which comprises:
    (a) an elemental analysis: C 62.73; H 7.60; N 1.00; O 28.67 (by difference);
    (b) a molecular weight of 1225 (FABMS);
    (c) a specific optical rotation: $[\alpha]_D^{26}=0$; (C 0.385, methanol);
    (d) a characteristic ultraviolet absorption spectra as shown in FIG. I of the attached drawings;
    (e) a characteristic infrared absorption spectrum as shown in FIG. II of the attached drawings;
    (f) a characteristic proton nuclear magnetic resonance as shown in FIG. III of the attached drawings; and
    (g) a characteristic carbon-13 nuclear magnetic resonance spectrum as shown in FIG. IV of the attached drawings.

2. The compound LL-E19020 BETA which comprises:
    (a) an elemental analysis: C 63.33; H 7.72; N 1.16; O 27.79 (by difference);
    (b) a molecular weight of 1225 (FABMS);
    (c) a specific optical rotation: $[\alpha]_D^{26}=-17\pm2$ (C 0.455, methanol);
    (d) characteristic ultraviolet absorption spectrum as shown in FIG. V of the attached drawings;
    (e) a characteristic infrared absorption spectrum as shown in FIG. VI of the attached drawings;
    (f) a characteristic proton nuclear magnetic resonance spectrum as shown in FIG. VII of the attached drawings; and
    (g) a characteristic carbon-13 nuclear magnetic resonance spectrum as shown in FIG. VIII of the attached drawings.

3. A method of treating bacterial infections in warm-blooded animals which comprises administering to said animals an antibacterially effective amount of antibiotic LL-E19020α as defined in claim 1.

4. A process for producing antibiotic LL-E19020α as defined in claim 1 which comprises aerobically fermenting the organisim Streptomyces lydicus ssp. tanzanius NRRL 18036 or mutants thereof in a liquid medium containing assimilable sources of carbon, nitrogen and inorganic salts, until substantial antibiotic activity is imparted to said medium and then recovering the antibiotic therefrom.

5. A process for producing antibiotic LL-E19020α as defined in claim 1 which comprises aerobically fermenting a liquid medium containing assimilable sources of carbon, nitrogen and inorganic salts, which medium has been inoculated with a viable culture of the organism Streptomyces lydicus ssp. tanzanius NRRL 18036 or mutants thereof, maintaining said fermentation culture at a temperature of 25°–32° C. for a period of about 90–200 hours, harvesting the mash and extracting the antibiotic.

6. A method of treating bacterial infections in warm-blooded animals which comprises administering to said animals an antibacterially effective amount of antibiotic LL-E19020β as defined in claim 2.

7. A process for producing antibiotic LL-19020β as defined in claim 2 which comprises aerobically fermenting the organisim Streptomyces lydicus ssp. tanzanius NRRL 18036 or mutants thereof in a liquid medium containing assimilable sources of carbon, nitrogen and inorganic salts, until substantial antibiotic activity is imparted to said medium and then recovering the antibiotic therefrom.

8. A process for producing antibiotic LL-19020β as defined in claim 2 which comprises aerobically fermenting a liquid medium containing assimilable sources of carbon, nitrogen and inorganic salts, which medium has been inoculated with a viable culture of the organism Streptomyces lydicus ssp. tanzanius NRRL 18036 or mutants thereof, maintaining said fermentation culture at a temperature of 25°–32° C. for a period of about 90–200 hours, harvesting the mash and extracting the antibiotic.

* * * * *